United States Patent
Weers

(10) Patent No.: US 10,822,547 B2
(45) Date of Patent: Nov. 3, 2020

(54) BASIC IONIC LIQUIDS AS HYDROCHLORIC ACID SCAVENGERS IN REFINERY CRUDE PROCESSING

(71) Applicant: Baker Hughes, a GE company, LLC, Houston, TX (US)

(72) Inventor: Jerry J. Weers, Richmond, TX (US)

(73) Assignee: Baker Hughes Holdings LLC, Houston, TX (US)

( * ) Notice: Subject to any disclaimer, the term of this patent is extended or adjusted under 35 U.S.C. 154(b) by 235 days.

(21) Appl. No.: 15/839,072

(22) Filed: Dec. 12, 2017

(65) Prior Publication Data

US 2019/0177622 A1    Jun. 13, 2019

(51) Int. Cl.

| C10G 7/00 | (2006.01) |
|---|---|
| C10G 7/10 | (2006.01) |
| C10G 19/02 | (2006.01) |
| C10G 75/02 | (2006.01) |
| C07C 211/63 | (2006.01) |
| C10G 53/12 | (2006.01) |

(52) U.S. Cl.
CPC .............. *C10G 7/10* (2013.01); *C07C 211/63* (2013.01); *C10G 19/02* (2013.01); *C10G 53/12* (2013.01); *C10G 75/02* (2013.01); *C10G 2300/80* (2013.01)

(58) Field of Classification Search
CPC .......... C10G 7/10; C10G 19/02; C10G 75/02; C10G 53/02; C10G 53/12; C10G 2300/80; C07C 211/62; C07C 211/63; C07C 211/64
See application file for complete search history.

(56) References Cited

U.S. PATENT DOCUMENTS

| 5,660,717 A | 8/1997 | Lindemuth |
|---|---|---|
| 6,013,175 A | 1/2000 | Weers et al. |
| 6,488,868 B1 | 12/2002 | Meyer |
| 6,599,445 B2 | 7/2003 | Meyer |
| 6,696,572 B2 | 2/2004 | Meyer |
| 7,918,905 B2 | 4/2011 | Kremer et al. |
| 8,177,962 B2 | 5/2012 | Koizumi et al. |
| 8,679,203 B2 | 3/2014 | O'Brien et al. |
| 9,394,617 B2 | 7/2016 | Hall et al. |
| 2006/0013798 A1 | 1/2006 | Henry et al. |
| 2006/0043340 A1* | 3/2006 | Koizumi ............ C02F 5/12 252/387 |
| 2015/0191659 A1* | 7/2015 | Anderson ............ C10G 31/08 204/168 |

OTHER PUBLICATIONS

NACE International, "Crude Distillation Unit-Distillation Tower Overhead System Corrosion", Publication 34109, 2009, 1-85.
Al-Omari, Ahmad S., et al., "Refinery Caustic Injection Systems: Design, Operation, and Case Studies", NACE International, Paper No. 08551, 2008, 1-16.
Rue, James R., et al., "Control of Salt-Initiated Corrosion in Crude Unit Overhead Systems", NACE International, Paper No. 01538, 2001, 1-11.
Coble, Nile D., "Corrosion Philosophy; Treat the Source, Not the Symptom", NACE International, Paper No. 01538, 2002, 1-8.
Chambers, Brian, et al., "Corrosion in Crude Distillation Unit Overhead Operations: A Comprehensive Review", NACE International, Paper No. 11360, 2011, 1-11.
Lonza Technical Data Sheet, "CARBOSHIELD 1000", 2008, 2 pages.

* cited by examiner

*Primary Examiner* — Prem C Singh
*Assistant Examiner* — Brandi M Doyle
(74) *Attorney, Agent, or Firm* — Mossman, Kumar & Tyler, P.C.

(57) ABSTRACT

Treatment of crude oil with basic ionic liquids (ILs), results in scavenging of any hydrochloric acid (HCl) that is present to remove the HCl. The IL is a quaternary ammonium compound having the formula $R_4N^+X^-$ or $R_3N^+R'N^+R_3$, where R is independently an alkyl group, an alkylbenzyl group, a hydroxyalkyl group, or a hydroxyalkylbenzyl group, and R is straight or branched and has 1-22 carbon atoms, R' is a straight or branched alkylene or oxyalkylene having 1 to 10 carbon atoms, and where $X^-$ is selected from the group consisting of hydroxide, carbonate, alkylcarbonate, bicarbonate or alkoxide, where the alkyl group of the alkyl-carbonate or alkoxide, if present, is straight or branched and has 1 to 8 carbon atoms. The ILs are introduced into the crude oil after the refinery desalters and before the crude distillation tower to prevent or inhibit HCl from distilling to the crude tower overhead.

12 Claims, No Drawings

BASIC IONIC LIQUIDS AS HYDROCHLORIC ACID SCAVENGERS IN REFINERY CRUDE PROCESSING

TECHNICAL FIELD

The present invention relates to the scavenging of hydrochloric acid from crude oil, and more particularly relates, in one non-limiting embodiment, to methods for scavenging hydrochloric acid from crude oil using basic ionic liquids to reduce crude tower overhead chloride.

TECHNICAL BACKGROUND

In a refinery, the neutralization of acids prior to the crude tower overhead condensing system using ammonia or organic amine neutralizers is a conventional practice. However, these neutralizers can be misapplied or recycled with water streams routed to the crude oil desalters. Consequently, corrosive chloride salts can form, which cause severe fouling and corrosion of tower trays, overhead vapor lines, and condensers. Various techniques may be effective to mitigate these problems including, but not necessarily limited to, crude oil desalting, caustic injection for overhead chloride control, water washing, filming amines, and more recently, adding low base strength neutralizers to control corrosive salt formation.

As refineries have needed to work with opportunity crudes, refinery operators have encountered substantial risk of corrosion damage in both the crude distillation unit (CDU) and the vacuum unit. The CDU is often exposed to increased levels of chlorides and sulfur species that lead to significant corrosion issues including, but not necessarily limited to, under deposit corrosion due to sublimating species such as ammonium chloride ($NH_4Cl$), aqueous corrosion due to hydrochloric acid (HCl) or acidic sulfur species, and/or fouling issues related to the build-up of sublimating species. Frequently the main cause for these problems may be correlated to high chloride content in the crude coming out of the desalter or inadequate controls to ensure that conditions for fractionation operations occur above the aqueous dew point.

Predicting and determining the contribution and severity of these corrosion problems is difficult because of the significant complexity of the chemistry involved. It would be desirable to find a method for scavenging HCl from crude oil before the crude reaches the distillation tower to prevent or mitigate corrosion in the tower.

SUMMARY

There is provided in one non-limiting embodiment a method for scavenging hydrochloric acid from crude oil containing the hydrochloric acid, where the method includes contacting the crude oil with an amount of a basic ionic liquid effective to react with the hydrochloric acid to scavenge the hydrochloric acid therefrom. The basic ionic liquid comprises a quaternary ammonium compound having the formula $R_4N^+X^-$ or $R_3N^+R'N^+R_3$, where R is independently an alkyl group, an alkylbenzyl group, a hydroxyalkyl group, or a hydroxyalkylbenzyl group, and R is straight or branched and has 1 to 22 carbon atoms, R' is a straight or branched alkylene or oxyalkylene having 1 to 10 carbon atoms, and where $X^-$ is selected from the group consisting of hydroxide, carbonate, alkylcarbonate, bicarbonate or alkoxide, where the alkyl group of the alkylcarbonate or alkoxide, if present, is straight or branched and has 1 to 8 carbon atoms.

DETAILED DESCRIPTION

It has been discovered that ionic liquids (ILs) may be used to neutralize HCl formed in the crude furnace due to hydrolysis of magnesium and calcium chloride at the high temperatures present. If not removed, the HCl will distill to the crude tower overhead system where it reduces pH and will cause corrosion to occur. The ionic liquids inhibit or prevent corrosion by scavenging the corrosion agent in the furnace so that the HCl never reaches the top of the tower. The ionic liquid reacts with HCl, or possibly even magnesium chloride ($MgCl_2$) or calcium chloride ($CaCl_2$), to keep the overhead system low in HCl content. The IL is introduced or injected into a location downstream of the refinery desalters and before or into the crude furnace, but the corrosion protection desired is further downstream in the crude tower overhead system. Multiple injection points are also acceptable. Because these ionic liquids are high boiling point materials that decompose under the high temperatures of the furnace, they will never distill to the tower top where the corrosion is occurring.

In short, the addition of the basic ionic liquids to the crude oil prior to the furnace, and/or directly into the furnace, in the atmospheric distillation unit reduces crude tower overhead chloride levels by scavenging HCl formed by hydrolysis of the salts present in the feedstock. The ionic liquids are a metal free alternative to the caustics (e.g. NaOH, KOH) currently used. These materials contribute alkali metals (e.g. Na, K) to the bottoms product coming from the crude tower. These metals are harmful to downstream units processing the residual oil and can contribute to unwanted ash in finished products. The ILs are strong bases and thus can form quaternary ammonium chlorides with the HCl. The substituent groups on the ILs can be chosen to provide the quaternary ammonium chlorides with the necessary stability and non-volatility to avoid the contamination of distillates and are less harmful than metals to downstream processes.

It should also be understood that the term "scavenged" also includes methods where HCl is removed from the crude but the total chlorine content of the crude oil is not reduced. That is, the reaction products of the ILs with the HCl stay in the crude oil. The treatment reacts the basic ILs with the HCl to give products that stay in the furnace.

In a non-limiting embodiment the basic ionic liquids include, but are not necessarily limited to, quaternary or diquaternary ammonium compound having the formula $R_4N^+X^-$ or $R_3N^+R'N^+R_3$, where R is independently an alkyl group, an alkylbenzyl group, a hydroxyalkyl group, or a hydroxyalkylbenzyl group, and R is straight or branched and has 1 to 22 carbon atoms, R' is a straight or branched alkylene or oxyalkylene having 1 to 10 carbon atoms and where $X^-$ is chosen from the group hydroxide, carbonate, alkylcarbonate, bicarbonate or alkoxide, where the alkyl group of the alkylcarbonate or alkoxide, if present, is straight or branched and has 1 to 8 carbon atoms. In some non-restrictive versions R may be alkylaryl or aryl. In the definition of $X^-$ where $X^-$ is alkyloxide or alkylcarbonate, the alkyl group may in particular be methyl, ethyl, or tert-butyl, in a particular non-limiting embodiment.

It will be appreciated that the term "ionic liquid" means that the quaternary amine additives are organic salts that are liquid at relatively low temperature. Most salts are solids, but ILs have different properties such as high flash points, good solvency for many other chemicals, and strong basicity if the anion is hydroxide, methoxide, etc.

The basic ionic liquid may further comprise a suitable liquid including, but not necessarily limited to, water, a mono or polyhydric alcohol having 1 to 8 carbon atoms, or an aromatic solvent. Suitable alcohol solvents include, but are not necessarily limited to, methanol, 2-ethylhexyl alcohol, ethanol, 2-propanol, glycerol, ethylene glycol, diethylene glycol, and combinations thereof. Suitable aromatic solvents include, but are not necessarily limited to, toluene, xylenes, Aromatic 100, Aromatic 150 or Aromatic 200 (commercial aromatic solvents), and combinations thereof. In one non-limiting embodiment, the ILs will most likely be formulated with water or an alcohol solvent; they will not often be formulated with both an alcohol and aromatic solvent in the same formulation. The proportion of the quaternary ammonium compound or diquaternary ammonium compound may range from about 10 vol % independently to about 100 vol % of the total IL; alternatively from about 20 vol % independently to about 50 vol %. The word "independently" as used with respect to a range herein means that any lower threshold may be used with any upper threshold to provide a suitable alternative range; in a non-limiting example a suitable alternative range is from about 25 vol % to about 50 vol %.

The basic ILs and the method of using them should have an absence of a surfactant or a soap. Some ILS with certain long alkyl groups can have substantial surfactancy which hurts separation of crude oil and ILS solution. Thus not all ILs are suitable for use in the present method. They should have low surfactancy. As previously mentioned, in one non-restrictive version, the method herein has an absence of added alkali metals. In a further non-limiting embodiment the method has an absence of an added halogen compound.

In more detail, the method described herein encompasses the use of ionic liquids (ILs) as additives which are introduced to crude oil to scavenge HCl. The additive can be applied like a scavenger where it converts HCl into a reaction product that is not corrosive. In this application, the reaction products formed by the scavenger stay in the crude oil in the furnace, but are nevertheless defined as "scavenged" for the purposes of the method described herein.

It should be emphasized that the ILs described herein are different from a simple quaternary amine corrosion inhibitors which are surfactants that forms a protective film on the metal surfaces. Such corrosion inhibitors are applied wherever one would expect corrosion to occur in a system and being film-forming, they require the additive, corrosion agents and metal surface being protected to all be located in the same place.

In the present method, the ionic liquid is a scavenger of the corrosion agent HCl in contrast to being a filmer and since the IL additive is added to the furnace, or prior to the furnace, and stays in the furnace area, it is not located in the top of the crude tower where corrosion is a concern. Being a method employing a scavenger that inhibits corrosion while not even being present in the location where the corrosion is occurring makes the present method unique.

The present IL additives work in an analogous fashion to caustic (e.g. NaOH, KOH, etc.) but by being non-metallic, organic compounds they will not contribute harmful metals to the residual oil (resid) coming from the bottom of the tower. The harmful impact these alkali metals have on further downstream processes often limits the amount of caustic that can be used. Downstream concerns often limit the amount of caustic additive to such a degree that not all the HCl is removed. With the present ILs, there are no alkali metals and thus the crude furnace may be treated with as much ionic liquid as needed to remove all the HCl.

As mentioned, contacting the crude oil with the basic ionic liquid is conducted after at least one refinery desalter and before a crude distillation tower, and the IL may be injected or introduced into the crude furnace directly. Thus, contacting the crude oil with the basic ionic liquid is conducted at a temperature between about 240° F. (about 116° C.) independently to about 750° F. (about 399° C.); alternatively between about 450° F. (about 204° C.) independently to about 600° F. (about 316° C.).

The effective amount of the basic ionic liquid used is any amount that is effective to bind up and/or react with, i.e. "scavenge", the HCl and at least partially convert it to a reaction product that inhibits or prevents corrosion in the crude tower overhead. More specifically, the dose of the IL will be stoichiometric with the amount of HCl formed by the hydrolysis of the magnesium or calcium chloride. Typically, the amount of these metal salts should only be from about 3 to about 10 ppm in the desalted crude going to the crude distillation tower. As noted, the suitable ionic liquids have widely varying molecular weights, thus expressing the IL dosage as a molar equivalence rather than a simple ppm ratio is more appropriate. One suitable molar ratio ranges from at least 1 molar equivalent of ionic liquid per chloride present up to 10 molar equivalents per chloride present in the crude oil; alternatively from 2 to 5 molar equivalents IL per chloride molar equivalents present. By "chloride present" is meant primarily hydrogen chloride (HCl, which is hydrochloric acid in aqueous solution), but also other chlorides present, including, but not necessarily limited to, magnesium chloride, calcium chloride, and the like.

In the foregoing specification, the invention has been described with reference to specific embodiments thereof, more specifically configurations, methods, and compositions for scavenging HCl from crude oil. However, it will be evident that various modifications and changes can be made thereto without departing from the broader scope of the invention as set forth in the appended claims. Accordingly, the specification is to be regarded in an illustrative rather than a restrictive sense. For example, the type of crude oil stream, the amounts and ratios of ionic liquids, quaternary ammonium compounds, solvents, reaction products, treatment procedures, reaction parameters including but not limited to temperature, and other components and/or conditions falling within the claimed parameters, but not specifically identified or tried in a particular method, are expected to be within the scope of this invention. Further, it is expected that the method may change somewhat from one application to another and still accomplish the stated purposes and goals of the methods described herein.

The present invention may suitably comprise, consist or consist essentially of the elements disclosed and may be practiced in the absence of an element not disclosed. For instance, there may be provided a method for scavenging hydrochloric acid from crude oil containing the hydrochloric acid, where the method comprises, consists essentially of, or consists of contacting the crude oil with an amount of a basic ionic liquid effective to react with the hydrochloric acid to scavenge the hydrochloric acid therefrom, where the basic ionic liquid comprises, consists essentially of, or consists of a quaternary ammonium compound having the formula $R_4N^+X^-$ or $R_3N^+R'N^+R_3$, where R is independently an alkyl group, an alkylbenzyl group, a hydroxyalkyl group, or a hydroxyalkylbenzyl group, and R is straight or branched and has 1 to 22 carbon atoms, R' is a straight or branched alkylene or oxyalkylene having 1 to 10 carbon atoms, and where X⁻ is selected from the group consisting of hydroxide, carbonate, alkylcarbonate, bicarbonate or alkoxide, where the alkyl group of the alkylcarbonate or alkoxide, if present, is straight or branched and has 1 to 8 carbon atoms.

As used herein, the terms "comprising," "including," "containing," "characterized by," and grammatical equivalents thereof are inclusive or open-ended terms that do not exclude additional, unrecited elements or method acts, but also include the more restrictive terms "consisting of" and "consisting essentially of" and grammatical equivalents thereof. As used herein, the term "may" with respect to a material, structure, feature or method act indicates that such is contemplated for use in implementation of an embodiment of the disclosure and such term is used in preference to the more restrictive term "is" so as to avoid any implication that other, compatible materials, structures, features and methods usable in combination therewith should or must be, excluded.

As used herein, the singular forms "a," "an," and "the" are intended to include the plural forms as well, unless the context clearly indicates otherwise.

As used herein, the term "and/or" includes any and all combinations of one or more of the associated listed items.

As used herein, relational terms, such as "first," "second," "top," "bottom," "upper," "lower," "over," "under," etc., are used for clarity and convenience in understanding the disclosure and do not connote or depend on any specific preference, orientation, or order, except where the context clearly indicates otherwise.

As used herein, the term "substantially" in reference to a given parameter, property, or condition means and includes to a degree that one of ordinary skill in the art would understand that the given parameter, property, or condition is met with a degree of variance, such as within acceptable manufacturing tolerances. By way of example, depending on the particular parameter, property, or condition that is substantially met, the parameter, property, or condition may be at least 90.0% met, at least 95.0% met, at least 99.0% met, or even at least 99.9% met.

As used herein, the term "about" in reference to a given parameter is inclusive of the stated value and has the meaning dictated by the context (e.g., it includes the degree of error associated with measurement of the given parameter).

What is claimed is:

1. A method for scavenging hydrochloric acid from crude oil containing the hydrochloric acid, the method comprising:
    contacting the crude oil with an amount of a basic ionic liquid effective to react with the hydrochloric acid to scavenge the hydrochloric acid therefrom; where:
    the basic ionic liquid consists of:
        a quaternary ammonium compound having the formula $R_4N^+X^-$ or $R_3N^+R'N^+R_3$, where:
            R is independently an alkyl group, an alkylbenzyl group, a hydroxyalkyl group, or a hydroxyalkylbenzyl group, and R is straight or branched and has 1 to 22 carbon atoms,
            R' is a straight or branched alkylene or oxyalkylene having 1 to 10 carbon atoms, and
            where X⁻ is selected from the group consisting of hydroxide, carbonate, alkylcarbonate, bicarbonate or alkoxide, where the alkyl group of the alkylcarbonate or alkoxide, if present, is straight or branched and has 1 to 8 carbon atoms; and
        a liquid selected from the group consisting of a monohydric or polyhydric alcohol having 1 to 8 carbon atoms, and an aromatic solvent.

2. The method of claim 1 where contacting the crude oil with the basic ionic liquid is conducted at a temperature between about 240° F. (about 116° C.) to about 750° F. (about 399° C.).

3. The method of claim 1 where contacting the crude oil with the basic ionic liquid is conducted by adding the basic ionic liquid to the crude oil, where the effective amount of the basic ionic liquid ranges from about 1 to about 10 molar equivalents of the basic ionic liquid per molar equivalent of chloride present.

4. The method of claim 1 where in the basic ionic liquid, when X⁻ is carbonate, the carbonate is selected from the group consisting of carbonate, alkylcarbonate, and bicarbonate.

5. A method for scavenging hydrochloric acid from crude oil containing the hydrochloric acid, the method comprising:
    contacting the crude oil with an amount of a basic ionic liquid effective to react with the hydrochloric acid to scavenge the hydrochloric acid therefrom; where the contacting is conducted at a location after at least one refinery desalter and before a crude distillation tower at a temperature between about 240° F. (about 116° C.) to about 750° F. (about 399° C.), where:
    the basic ionic liquid consists of:
        a quaternary ammonium compound having the formula $R_4N^+X^-$ or $R_3N^+R'N^+R_3$, where:
            R is independently an alkyl group, an alkylbenzyl group, a hydroxyalkyl group, or a hydroxyalkylbenzyl group, and R is straight or branched and has 1 to 22 carbon atoms,
            R' is a straight or branched alkylene or oxyalkylene having 1 to 10 carbon atoms, and
            where X⁻ is selected from the group consisting of hydroxide, carbonate, alkylcarbonate, bicarbonate or alkoxide, where the alkyl group of the alkylcarbonate or alkoxide, if present, is straight or branched and has 1 to 8 carbon atoms; and
        a liquid selected from the group consisting of a monohydric or polyhydric alcohol having 1 to 8 carbon atoms, and an aromatic solvent.

6. The method of claim 5 where contacting the crude oil with the basic ionic liquid is conducted by adding the basic ionic liquid to the crude oil, where the effective amount of the basic ionic liquid ranges from about 1 to about 10 molar equivalents of the basic ionic liquid per molar equivalent of chloride present in the crude oil.

7. The method of claim 5 where in the basic ionic liquid, when X⁻ is carbonate, the carbonate is selected from the group consisting of carbonate, alkylcarbonate, and bicarbonate.

8. A method for scavenging hydrochloric acid from crude oil containing the hydrochloric acid, the method comprising:
    contacting the crude oil with an amount of a basic ionic liquid effective to react with the hydrochloric acid to scavenge the hydrochloric acid therefrom; where:
    the basic ionic liquid consists of:
        a quaternary ammonium compound having the formula $R_4N^+X^-$ or $R_3N^+R'N^+R_3$, where:
            R is independently an alkyl group, an alkylbenzyl group, a hydroxyalkyl group, or a hydroxyalkylbenzyl group, and R is straight or branched and has 1 to 22 carbon atoms,
            R' is a straight or branched alkylene or oxyalkylene having 1 to 10 carbon atoms, and
            where X⁻ is selected from the group consisting of hydroxide, carbonate, alkylcarbonate, bicarbonate or alkoxide, where the alkyl group of the alkylcarbonate or alkoxide, if present, is straight or branched and has 1 to 8 carbon atoms;

the basic ionic liquid further comprises a liquid selected from the group consisting of water, a monohydric or polyhydric alcohol having 1 to 8 carbon atoms, and an aromatic solvent; and contacting the crude oil with the basic ionic liquid is conducted by adding the basic ionic liquid to the crude oil, where the effective amount of the basic ionic liquid ranges from about 1 to about 10 molar equivalents of the basic ionic liquid per molar equivalent of chloride present.

9. The method of claim 8 where contacting the crude oil with the basic ionic liquid is conducted at a temperature between about 240° F. (about 116° C.) to about 750° F. (about 399° C.).

10. The method of claim 8 where in the basic ionic liquid, when $X^-$ is carbonate, the carbonate is selected from the group consisting of carbonate, alkylcarbonate, and bicarbonate.

11. The method of claim 1 further comprising, prior to the contacting, forming the hydrochloric acid by hydrolysis of a chloride selected from the group consisting of organic chlorides and inorganic chlorides.

12. The method of claim 11 further comprising, prior to the contacting, forming the hydrochloric acid by hydrolysis of a chloride selected from the group consisting of magnesium chloride and calcium chloride.

\* \* \* \* \*